(12) United States Patent
Buisker et al.

(10) Patent No.: US 7,411,206 B2
(45) Date of Patent: * Aug. 12, 2008

(54) METHOD AND SYSTEM FOR DETECTING THE POSITION OF AN EDGE OF A WEB

(75) Inventors: Raymond A. Buisker, Madison, WI (US); Andrew Kalnajs, Madison, WI (US)

(73) Assignee: Accuweb, Inc, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/484,324

(22) Filed: Jul. 11, 2006

(65) Prior Publication Data

US 2007/0029514 A1 Feb. 8, 2007

Related U.S. Application Data

(63) Continuation of application No. 10/358,987, filed on Feb. 5, 2003, now Pat. No. 7,075,099.

(51) Int. Cl.
*G01N 21/86* (2006.01)
*G01V 8/00* (2006.01)

(52) U.S. Cl. .................. 250/559.36; 356/637; 356/429; 250/239

(58) Field of Classification Search ............ 250/559.01, 250/559.29, 559.36, 559.12, 559.13, 559.15, 250/216, 236, 548, 221; 356/635–638, 429
See application file for complete search history.

(56) References Cited

U.S. PATENT DOCUMENTS

| 3,724,958 | A | 4/1973 | Callan |
| 4,110,627 | A | 8/1978 | Isherwood |
| 4,555,633 | A | 11/1985 | Björkelund |
| 4,559,451 | A | 12/1985 | Curl |
| 4,559,452 | A | 12/1985 | Igaki et al. |
| 5,072,414 | A | 12/1991 | Buisker et al. |
| 5,118,195 | A | * | 6/1992 | Dobbie ....................... 356/430 |
| 5,274,573 | A | 12/1993 | Buisker et al. |

(Continued)

FOREIGN PATENT DOCUMENTS

JP 04169452 A 6/1992

*Primary Examiner*—Georgia Epps
*Assistant Examiner*—Suezu Ellis
(74) *Attorney, Agent, or Firm*—Brinks Hofer Gilson & Lione

(57) ABSTRACT

A method and system for determining the lateral position of an edge of a web are disclosed. The system includes an array of light transmitting elements and a corresponding array of lenses and an array of light receiving elements and a corresponding array of lenses. The light transmitting elements are each paired with a light receiving element and the light transmitting elements each transmit a beam of light energy towards the corresponding receiving element. The beams of light can be occluded by a web passing between the transmitting elements and the receiving elements, thereby reducing the light received by the receiving elements. The receiving elements can generate a signal that is proportional to the amount of they receive, and a controller can be used to determine the lateral position of an edge of the web in response to the signals generated by the receivers. A compensation light beam can be employed to enable the controller to compensate for several factors that can affect measurement accuracy.

36 Claims, 12 Drawing Sheets

U.S. PATENT DOCUMENTS

| | | |
|---|---|---|
| 5,637,040 A * | 6/1997 | Kim et al. .................. 454/256 |
| 5,834,877 A | 11/1998 | Buisker et al. |
| 5,932,888 A | 8/1999 | Schwitzky |
| 6,175,419 B1 | 1/2001 | Haque et al. |
| 6,323,948 B2 | 11/2001 | Haque et al. |

* cited by examiner

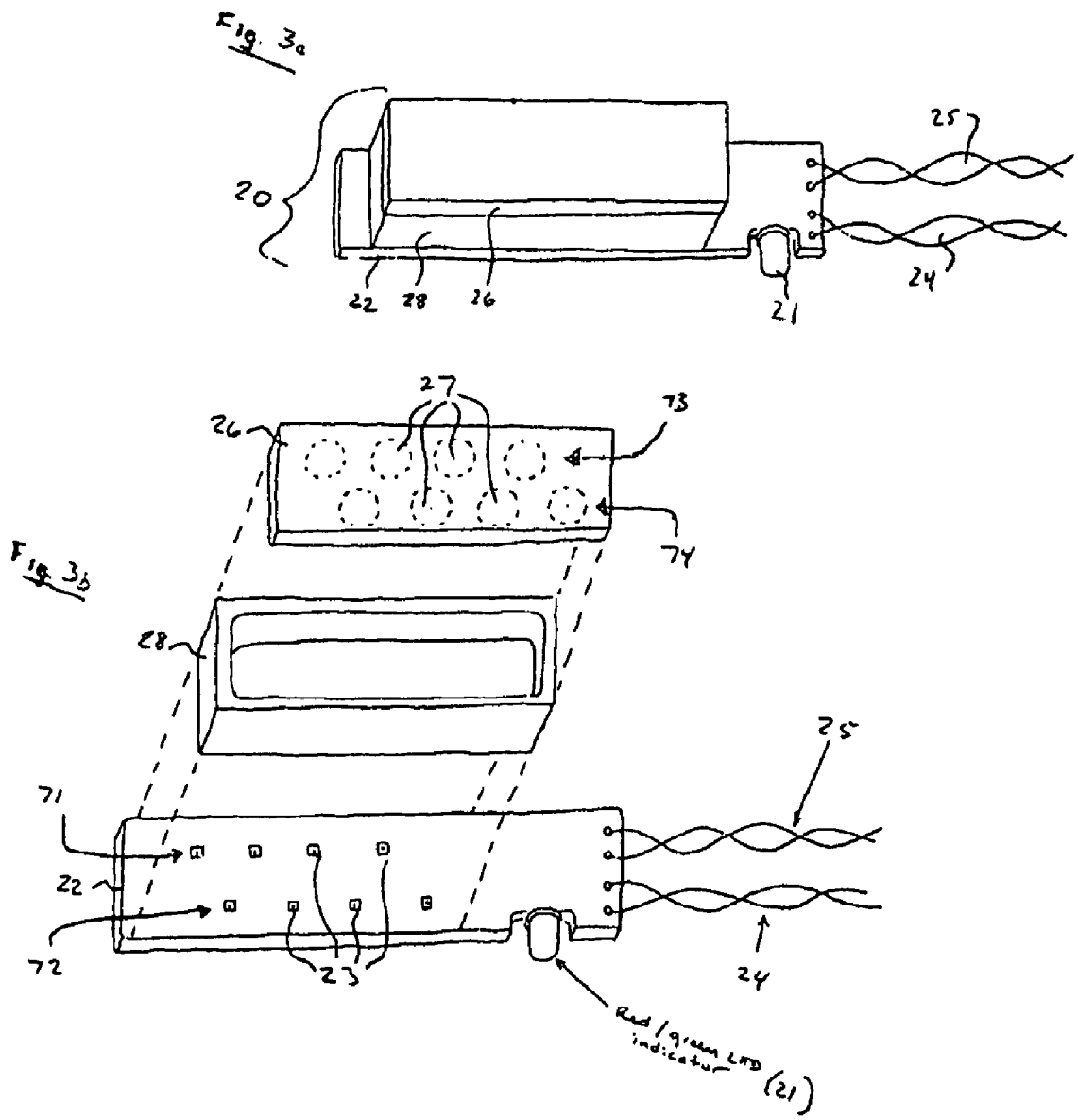

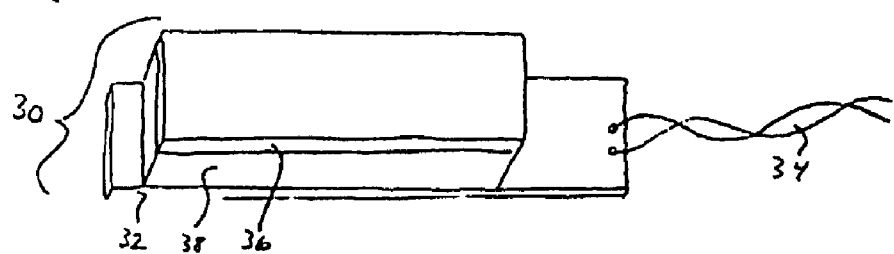
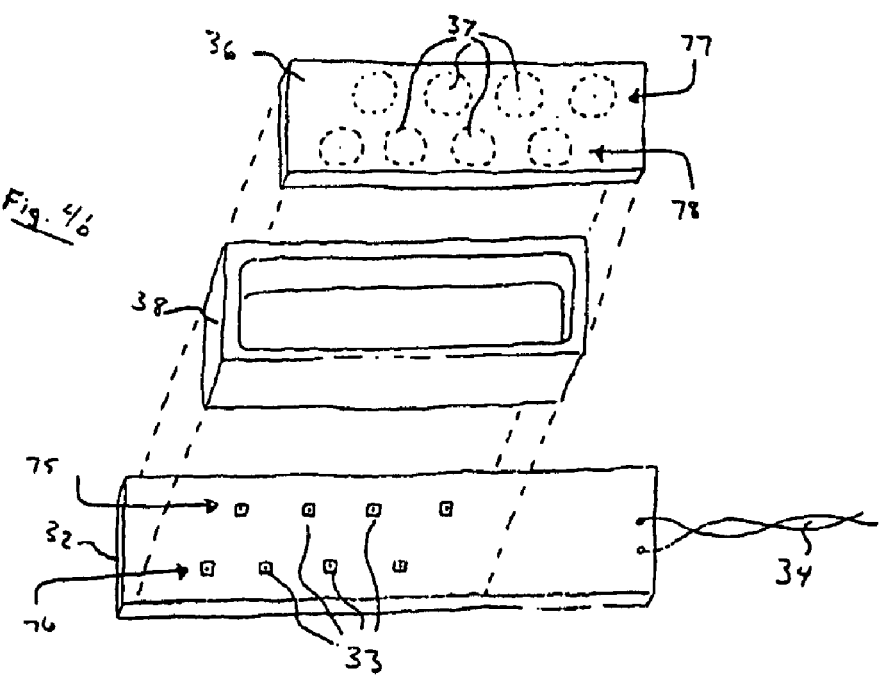

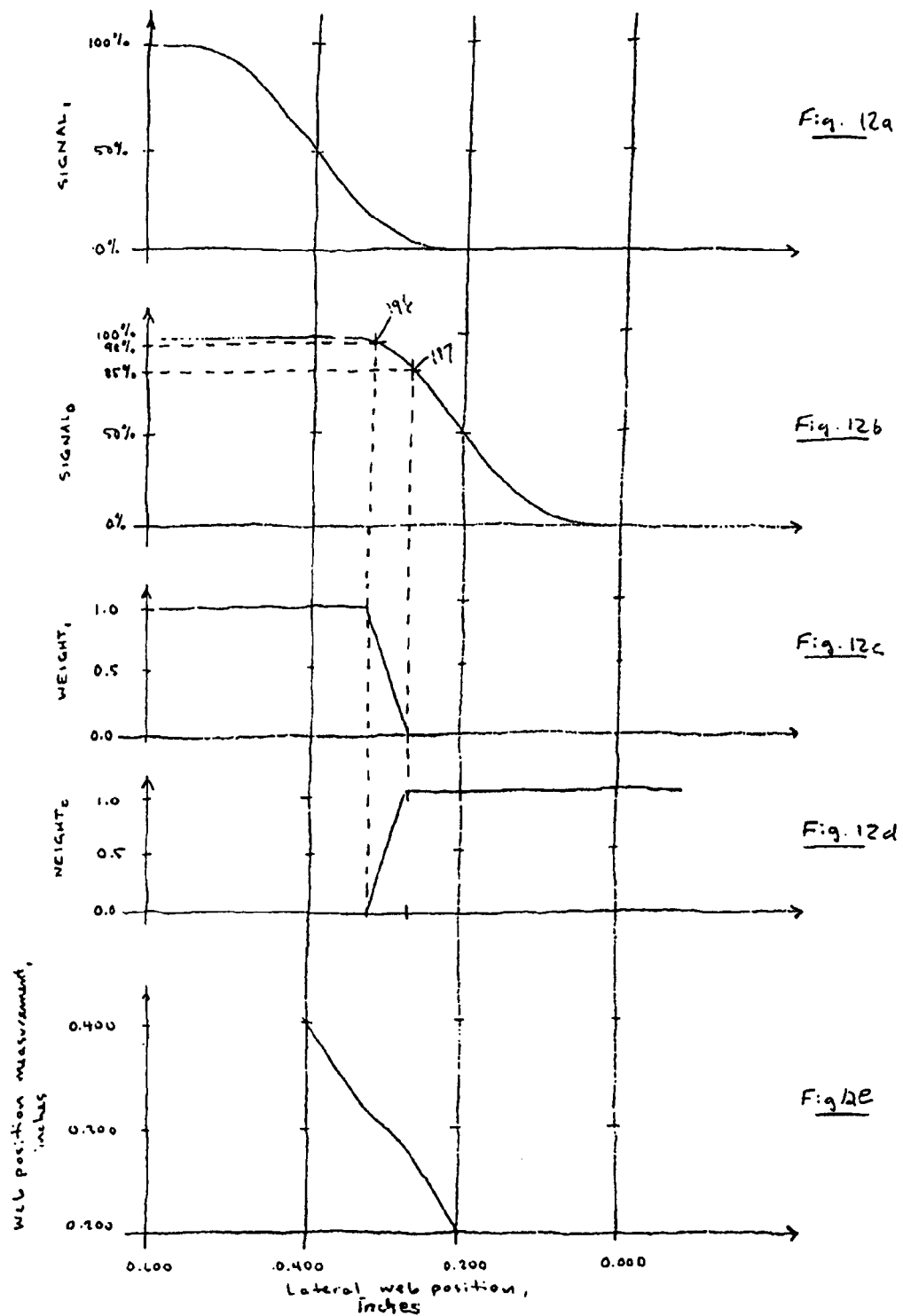

METHOD AND SYSTEM FOR DETECTING THE POSITION OF AN EDGE OF A WEB

This application is a continuation of prior application Ser. No. 10/358,987, filed Feb. 5, 2003, now U.S. Pat. No. 7,075,099, which is incorporated by reference herein.

FIELD OF THE INVENTION

The present invention relates generally to guiding a moving web and more particularly to a system and method for determining the position of an edge of a web.

BACKGROUND

Many different types of materials including fabric, paper, films, foils, and the like are formed into what is commonly known as a web. In the production, processing, or treatment of a web, the web is often moving as it progresses from one operation, such as cutting, slitting, printing, and the like, to the next operation. It is important to be able to accurately determine the position of the web as it moves so that it can be properly aligned for the various operations.

One commonly known technique for determining the position of a moving web involves detecting the position of the physical edge of the web using an ultrasonic edge detector. Several such edge detectors are described in U.S. Pat. Nos. 5,072,414, 5,274,573, and 5,834,877, all to Buisker et al. These patents all describe compact edge detectors that allow for the use of a compensation beam in addition to the position detecting beams. Despite their advantages, these edge detectors cannot be used to determine the position of webs that consist of certain types of materials that are acoustically transparent, such as non-woven fabric and mesh.

Other types of edge detectors that utilize light-type edge detectors are also known. One such edge detector is described in U.S. Pat. Nos. 6,175,419 and 6,323,948, both to Haque et al. While this system utilizes light sources, the system also includes a complex housing design and a complex lens system that is not compact in design.

A system and method for determining the position of an edge of a web that overcome these deficiencies are needed.

BRIEF DESCRIPTION OF THE DRAWINGS

FIG. 3a is a perspective view of a transmitter assembly of a preferred embodiment.

FIG. 3b is an exploded view of the transmitter assembly of FIG. 3a.

FIG. 4a is a perspective view of a receiver assembly of a preferred embodiment.

FIG. 4b is an exploded view of the receiver assembly of FIG. 4a.

FIG. 12a is a graphical depiction of a received signal strength for a single light receiver as compared to a lateral position of an edge of a web of a preferred embodiment FIG. 12b is a graphical depiction of received signal strengths for two light receiver as compared to a lateral position of an edge of a web of a preferred embodiment FIG. 12c is a graphical depiction of a weighting scale for one light receiver of a preferred embodiment.

FIG. 12d is a graphical depiction of a weighting scale for a second light receiver of a preferred embodiment FIG. 12e is a graphic depiction of a calculated lateral position of an edge of a web as compared to an actual lateral position of an edge of a web.

DETAILED DESCRIPTION OF THE PRESENTLY PREFERRED EMBODIMENTS

By way of introduction, the preferred embodiments described herein include systems and methods for determining the position of an edge of a web or sheet of material in a manufacturing or converting process. In one embodiment, a light transmitter assembly is used to transmit optical energy, preferably in the form of a plurality of light beams, that can be received by a light receiver assembly to sense the position of a web. The light transmitter assembly preferably comprises an array of light transmitting elements and a corresponding array of lenses, and the light receiver assembly preferably comprises an array of light receiving elements and a corresponding array of lenses. The light transmitting elements are each paired with a light receiving element, and the light transmitting and receiving elements are located opposite one another on opposite sides of the web plane near the edge of the web.

In typical use and operation the web passes between the light transmitting elements and the receiving elements such that the web occludes some of the light beams generated between the light emitting elements and the light receiving elements. Typically, the web fully occludes some of the beams of light, partially occludes some of the beams of light, and does not occlude the remaining beams of light. Preferably, a controller sequentially activates one of the transmitting elements and one of the light receiving elements so that a light beam is generated between the activated light transmitting element and the activated light receiving element. The light receiving elements can receive un-occluded light that is transmitted from the corresponding light transmitting elements. For the beams of light that are partially occluded, the amount of light energy striking the receiving element will be reduced, in proportion to the amount of occlusion, as compared to an un-occluded light beam. The receiving elements generate a signal that is proportional to the amount of energy striking it. Since the amount of occlusion is proportional to the position of the web's edge with respect to a reference point, the signal generated by the receiver assembly will also be proportional to the position of the edge. A controller can be used to determine the position of an edge of the web in response to the signal generated by the receiver assembly. Also, a compensation light beam can be employed to enable the controller to compensate for several factors that can affect measurement accuracy.

The resulting system is compact in design and enables the position of the edge of the web to be accurately determined. These system and methods are preferably used with web materials that are optically opaque or semi-opaque such as paper, woven and non-woven fabrics, some plastic films, and metal foils.

Figure 1:
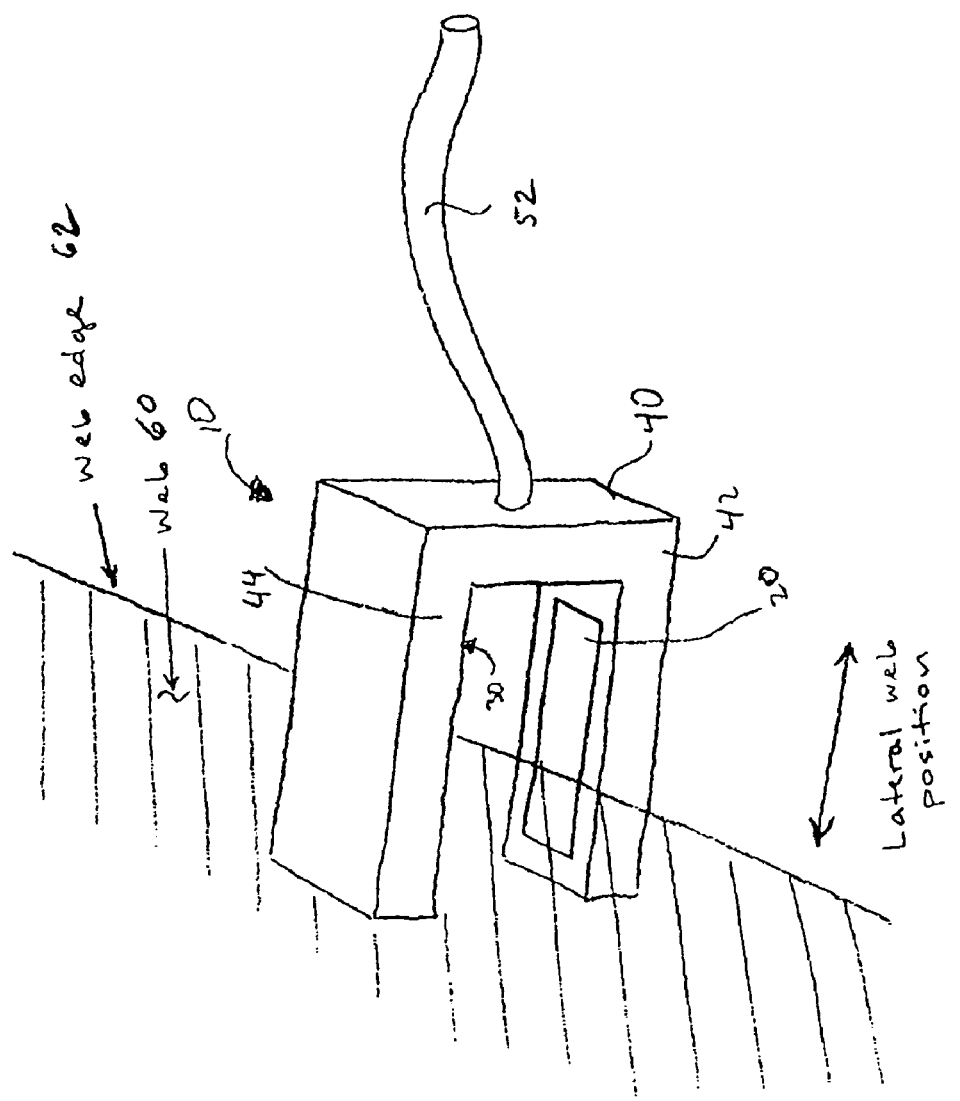
FIG. 1 is a perspective view of an edge detector assembly of a preferred embodiment.
Figure 2:
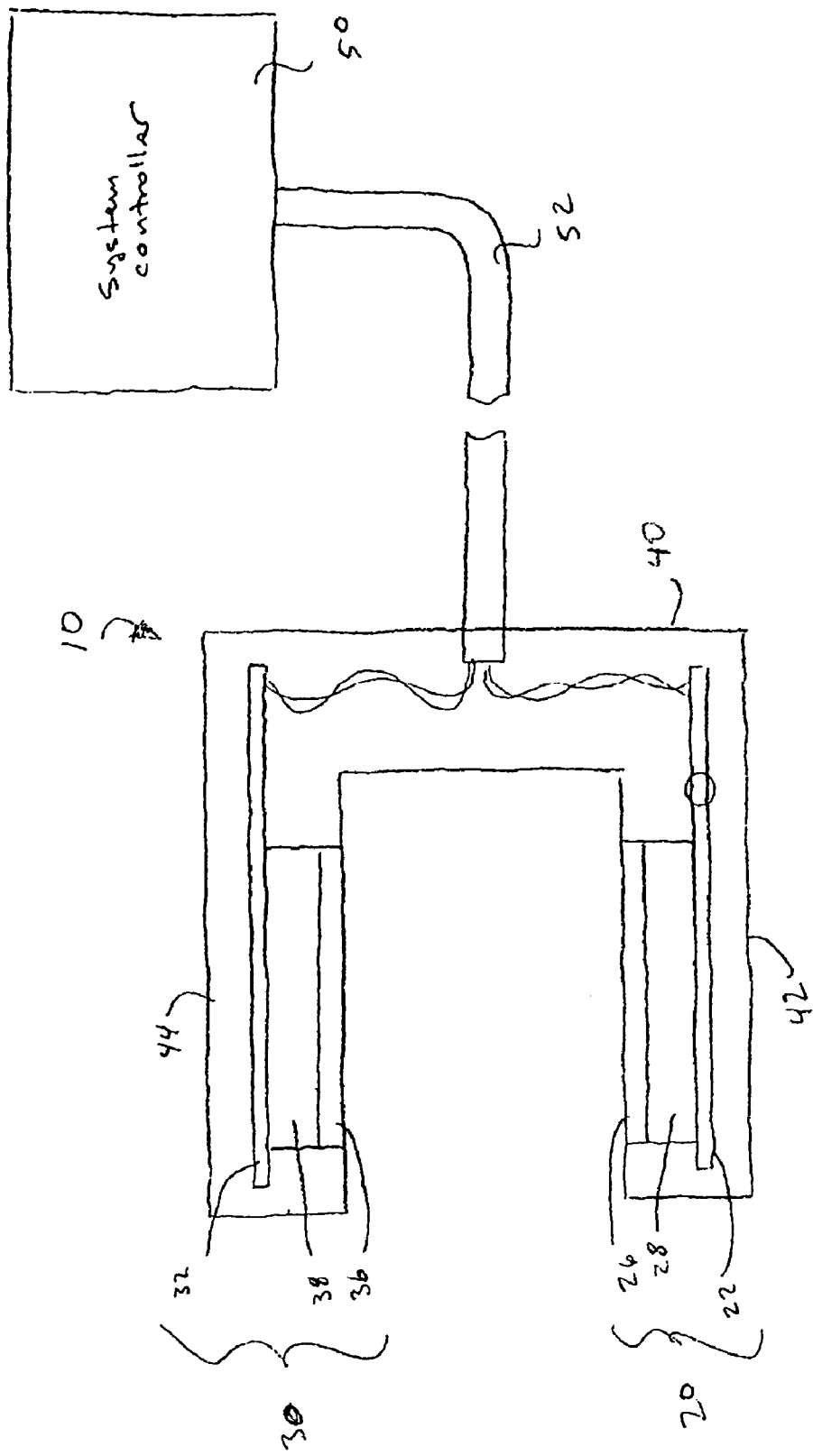
FIG. 2 is a cross-sectional view of the edge detector assembly of FIG. 1.

By way of example, FIGS. 1 and 2 depict an edge detector assembly 10 of a preferred embodiment. The edge detector assembly 10 comprises a transmitter assembly 20, a receiver assembly 30, and a housing 40. The transmitter assembly 20 preferably comprises a transmitter circuit board 22, a transmitter lens assembly 26, and a transmitter spacer 28, as explained in more detail below. The receiver assembly 30 preferably comprises a receiver circuit board 32, a receiver lens assembly 36, and a receiver spacer 38, as explained in more detail below.

The housing 40 is preferably "U" shaped and includes a lower arm 42 and an upper arm 44 with a gap between the arms 42, 44. The transmitter assembly 20 is preferably disposed in the lower arm 42 and the receiver assembly 30 is preferably disposed in the upper arm 44, but the location of the two assemblies can be reversed. The preferred "U" shape of the housing 40 enables a portion of the web of material 60 to pass through the gap between the lower arm 42 and the upper arm 44. The preferred size of the gap between the lower arm 42 and the upper arm 44 can range from less than one inch to over four inches in width. However, larger gaps can also be used, depending upon the application.

The lower and upper arms 42, 44 are preferably made in lengths that range from less than one inch to over twenty inches long to accommodate the expected range of lateral web movement. However, other longer lengths can also be made. The housing 40 is preferably constructed from aluminum, but any suitable material, including stainless steel, other metals, plastics, and composites can be used. In an alternative configuration, suitable for very long edge detectors that lack sufficient mechanical rigidity to be self-supporting, the housing can be formed so that it is closed at both ends. Use of this configuration is limited to webs narrower than the distance between the end supports. In further alternative embodiments, housings of varying shapes and sizes can be used and one or more housing sections can be used. For example, the transmitter assembly 20 and the receiver assembly 30 can be disposed in separate housings that are not connected. A black anodized coating is preferably applied to all surfaces of the housing 40 to protect the housing 40 from corrosion and to absorb stray light.

A system controller 50 is preferably coupled with the edge detector assembly 10 by way of a cable 52 or other communication link to facilitate communication of control and measurement information, as explained in more detail below. A cable link can be supplied in lengths up to several hundred feet depending on the relative locations of the edge detector assembly 10 and the system controller 50. The preferred cable link comprises three sets of twisted pair wires, as described in more detail below. Alternatively, other communication links, such as fieldbus networks, including CAN bus and DeviceNet, Radio Frequency (RF), Infrared, and Microwave communications links can be used to enable communication between the controller 50 and the edge detector assembly 10.

In general, the system controller 50 can transmit control signals to the transmitter assembly 20 and the receiver assembly 30 to control the activation of both the transmitter assembly 20 and the receiver assembly 30, as described in more detail below. The system controller can receive a data signal from the receiver assembly 30 and can analyze the data signal to determine the position of the edge of the web, as described in more detail below. The system controller 50 preferably comprises a microcontroller that is responsive to a software program, as described in more detail below.

Referring now to FIGS. 3a and 3b, a preferred embodiment of the transmitter assembly 20 is shown. The transmitter assembly 20 preferably comprises a transmitter circuit board 22 that serves as a monolithic mounting substrate for, and allows interconnection of, all of the transmitter components, including a plurality of light sources 23, an indicator 21, and signal processing circuits (not shown). The transmitter circuit board 22 also provides a mounting base for an optics system that includes the lens array 26 and the transmitter spacer 28, which joins the lens array 26 to the transmitter circuit board 22. The transmitter circuit board 22 also includes lands or pads (not shown) that enable the transmitter elements, including the plurality of light sources 23 to be surface-mounted on the transmitter circuit board 22. The shape and dimensions of the lands or pads are preferably optimized so that they are nearly or exactly the same size as the light sources 23. This reduces possible lateral movement or drift of the light sources during a reflow soldering process. While a single circuit board is preferably used, various types, configurations, and numbers of circuit boards can be used.

The plurality of light sources 23 are preferably arranged in a staggered pattern to allow a degree of overlap between the lateral transmitting ranges of adjacent light sources. However, other arrangements, including arrangements having various amounts of lateral and longitudinal overlap and linear arrangements, can be used. The plurality of light sources 23 preferably comprise gallium-aluminum-arsenide (GaAlAs) light emitting diodes (LEDs). The plurality of light sources 23 preferably emit infrared light when activated and have a peak emission at a wavelength of approximately 890 nanometers (nm). However, other wavelengths can also be used. In alternative embodiments, the plurality of light sources can comprise any type of modulateable light source, including light emitting diodes (LED), lasers, and the like or combinations thereof.

The lens assembly 26 preferably comprises a plurality of lenses 27 that are formed into a single piece of material. In a preferred embodiment, the plurality of lenses 27 comprise aspheric positive focal length fresnel lenses that are formed into a plastic sheet by compression-molding. The plastic sheet is preferably composed of an acrylic plastic. A scratch and chemical resistant coating is preferably applied to the exterior surface of the lens assembly 26 to increase the durability of the lenses 27. The plurality of lenses 27 are preferably arranged in the staggered pattern that mirrors the staggered pattern of the plurality of light sources 23 so that each of the plurality of lens 27 substantially lines up on an axis with a corresponding light source 23. However, other arrangements, including arrangements having various amounts of overlap and linear arrangements, can be used. In further alternatives, different types of lenses, including spherical lenses, plano-convex lenses, and bi-convex lenses can be used. Also, the lens assembly 26 can be formed using various manufacturing techniques and can be formed using various types of material, including various types of plastic and glass.

The transmitter spacer 28 provides a mounting surface for the lens array 26 and is of a thickness sufficient to place the plurality of light sources 23 at the focal point of the lenses 27. The transmitter spacer 28 preferably comprises an epoxy-glass composite and is attached to transmitter circuit board 22 by epoxy adhesive. Alteratively, the transmitter spacer can be formed from various plastics, metals, wood, composites, and the like and can be connected to the circuit board by various adhesives, bonding techniques, and mechanical fasteners such as screws. In alternative embodiment, various types and numbers of spacers can be used.

The indicator 21 preferably comprises a red/green light emitting diode that provides a visual indication to a user or operator of the status of the edge detector assembly 10. The indicator preferably is off or displays no color if the web edge is in a preferred range of positions, displays red if the web edge is positioned to one side of the preferred range, and displays green if the web edge is positioned to the other side of the preferred range. In alternative embodiments, the indicator 21 can comprise any type of visual, audible, or other types of indicators, such as lights, displays, a liquid crystal display, a vacuum fluorescent display, an electro-luminescent display, a CRT display, a field-emission display, buzzers, alarms, and the like.

Twisted pair wires 24, 25 preferably connect the transmitter assembly 20 with the system controller 50 and function as communication links. One communication link 24 is preferably dedicated to controlling the indicator 21, while the other communication link 25 is preferably dedicated to other transmitter assembly functions, as described in more detail below. In alternative embodiments, other types of communications links can be used and varying numbers of communications links can also be used.

Referring now to FIGS. 4a and 4b, a preferred embodiment of the receiver assembly 30 is shown. The receiver assembly 30 preferably comprises a receiver circuit board 32 that serves as a monolithic mounting substrate for, and allows interconnection of, all of the receiver components, including a plurality of light receivers 33 and signal processing circuits (not shown). The receiver circuit board 32 also provides a mounting base for an optics system that includes the lens array 36 and the receiver spacer 38 that joins the lens array 36 to the receiver circuit board 32. The receiver circuit board 32 also includes lands or pads (not shown) that enable the receiver components, including the plurality of light receivers 33 to be surface-mounted on the receiver circuit board 32. The shape and dimensions of the lands or pads are preferably optimized so that they are nearly or exactly the same size as the light receivers 33. This reduces possible lateral movement or drift of the light receivers during a reflow soldering process. While a single circuit board is preferably used, various types, configurations, and numbers of circuit boards can be used.

The plurality of light receivers 33 are preferably arranged in a staggered pattern that mirrors the staggered pattern of the plurality of light sources 23 so that each of the plurality of light receivers 33 is substantially on an axis that lines up with a corresponding light source 23. However, other arrangements, including arrangements having various amounts of overlap and linear arrangements, can be used. The plurality of light receivers 33 preferably respond to a broad range of wavelengths extending from visible to near-infrared, but are most sensitive to the light source's infrared emissions. Silicon photodiodes are the preferred light receiver because of their speed of response, spectral sensitivity, and temperature-stability, but any suitable light receiver, including photodiodes, phototransistors, a charge-coupled device (CCD), a CMOS imaging device, or the like, can be used. For example, phototransistors having an external connection to the base junction on the phototransistor die can be used with the present embodiments.

The lens assembly 36 preferably comprises a plurality of lenses 37 that are formed into a single piece of material. In a preferred embodiment, the plurality of lenses 37 comprise aspheric positive focal length fresnel lenses that are formed into a plastic sheet by compression-molding. The plastic sheet is preferably composed of an acrylic plastic that is opaque to visible wavelengths of light but is transparent to the 890 nm infrared wavelength used by the light sources 23 and light receivers 33. This characteristic reduces interference from artificial and natural lighting that may be present in the vicinity of the edge detector. A scratch and chemical resistant coating is preferably applied to the exterior surface of the lens assembly 36 to increase the durability of the lenses 37. The plurality of lenses 37 are preferably arranged in the staggered pattern that mirrors the staggered pattern of the plurality of light sources 23 and the plurality of light receivers 33 so that each of the plurality of lenses 37 is substantially on an axis that lines up with a corresponding light source 23 and light receiver 33. However, other arrangements, including arrangements having various amounts of overlap and linear arrangements, can be used. In further alternatives, different types of lenses, including spherical lenses, piano-convex lenses, and bi-convex lenses can be used. Also, the lens assembly 36 can be formed using various manufacturing techniques and can be formed using various types of material, including various types of plastic and glass.

One advantage of the preferred lens assemblies 26, 36 is that the monolithic design facilitates mounting of the lens assemblies 26, 36 during the assembly process. For example, the lens assemblies 26, 36 can be readily and accurately positioned, with respect to the light sources or light receivers, using a single spacer for each lens assembly. Also, the design of the lens assemblies 26, 36 allow for the use of spacers having a relatively simple design. In addition, the lens assemblies 26, 36 can be interchangeable with one another.

The receiver spacer 38 provides a mounting surface for the lens array 36 and is of a thickness sufficient to place the plurality of light receivers 33 at the focal point of the lenses 37. The receiver spacer 38 preferably comprises an epoxy-glass composite and is attached to the receiver circuit board 32 by epoxy adhesive. Alternatively, the receiver spacer can be formed from various plastics, metals, wood, composites, and the like and can be connected to the circuit board by various adhesives, bonding techniques, and mechanical fasteners such as screws. In alternative embodiment, various types and numbers of spacers can be used.

Twisted pair wires 34 preferably connect the receiver assembly 30 with the system controller 50 and function as a communication link. The communication link 34 preferably enables the exchange of all receiver control and measurement information, as described in more detail below. In alternative embodiments, other types of communications links can be used and varying numbers of communications links can also be used.

Figure 5:
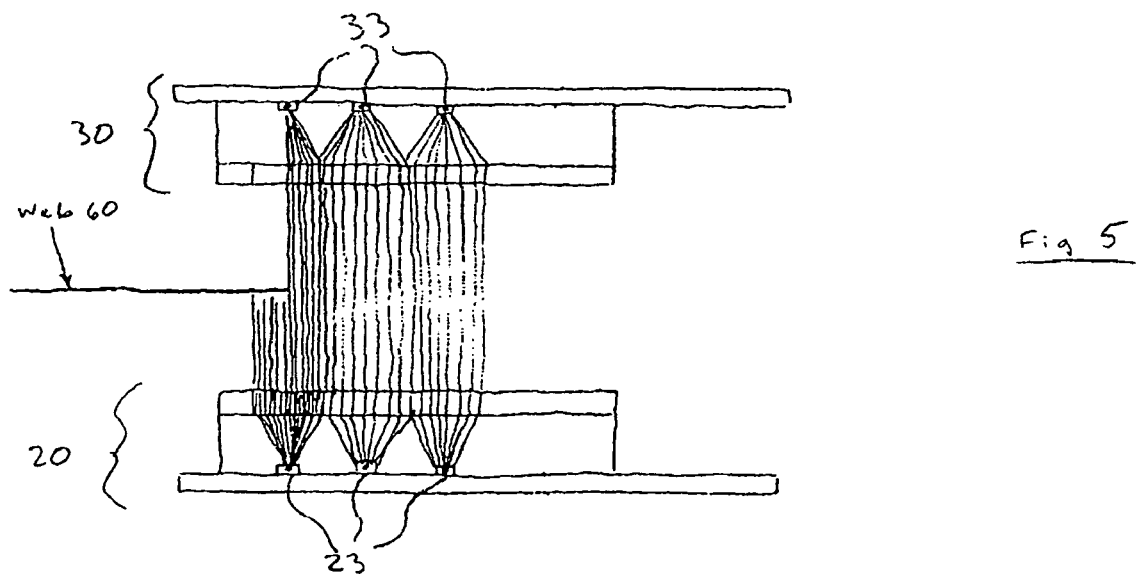
FIG. 5 is a side view of an edge detector assembly of a preferred embodiment.

As shown in FIG. 5, edge detector assembly 10 preferably comprises a plurality of light sources 23 and a corresponding plurality of light receivers 33 that operate in pairs to extend the lateral position-sensing range beyond that of a single pair. A "pair" generally consists of a light source and a light receiver that operate in conjunction with one another. This arrangement may be referred to herein as a "pair" or a "transmitter-receiver pair." These pairs are preferably arranged in a staggered pattern, as shown more clearly in FIGS. 3b and 4b, to create a degree of overlap between the lateral sensing ranges of adjacent transmitter-receiver pairs. This overlap is desirable, in most applications, because the useable sensing range of each individual transmitter-receiver pair can be slightly less than the lateral width of the corresponding light beam and/or of the lenses and other components from which it is constructed. A purely linear arrangement of transmitter-receiver pairs can result in a region between each adjacent pair where no sensing occurs, and the accuracy of position measurements derived from such an arrangement could degrade whenever the web's edge was within the transitional region between pairs.

The preferred staggered arrangement of the transmitter-receiver pairs, as shown in FIGS. 3a, 3b, 4a, and 4b, provides some overlap between the sensing ranges of adjacent pairs through the use of two substantially parallel, linear rows 71, 72 of equally-spaced light sources. The lateral position (left to right in the drawings) of one row 71 is offset from the second row 72 by a distance equal to one half the pair-to-pair spacing within a row. The longitudinal position (top to bottom in the drawings) of one row 71 is also offset from the second row 72. In this arrangement adjacent pairs are located in opposite rows—that is, pair 1 is in row 71, pair 2 is in row 72, pair 3 is in row 71, pair 4 is in row 72, etc. In this preferred embodiment, the plurality of lenses 27, the plurality of light receivers 33, and the plurality of lenses 37 are also arranged in two substantially parallel lines as shown by reference numbers 73-74, 75-76, and 77-78, respectively. In alternative embodiments, other staggered arrangements and spacing configurations can be used. For example, the spacing between pairs in the same row and the spacing between the rows can be altered. Also the lateral and longitudinal offset can be varied. Also, additional rows and additional pairs within a row can be added.

The edge detector assembly 10 is preferably connected to a system controller 50 by a link 52, as shown in FIG. 2 and described above. A preferred embodiment of the system controller 50 is shown in more detail in FIG. 6. The system controller 50 preferably includes the components that enable higher-order control and signal processing functions. These components include an analog line receiver 101, digital line drivers 102, 103, 104, a digital amplifier 105, a band-pass filter 107, a peak-detector 109, an analog-to-digital converter 110, a microcontroller 111 having program memory 112 and data memory 113, a non-volatile read-write memory 114, a clock operator 115, a reset generator 116, an operator interface 117 and analog and digital I/O 118. While the system controller 50 preferably comprises a microcontroller, any suitable controller, microprocessor, or processor, as known to those skilled in the art can be use. Also, the system controller can be one or more than one component, as the functionality of the controller can be distributed among several components in the system.

Three twisted-pair cables 24, 25, 34 are also connected to the system controller 50. One pair 34 is dedicated to the receiver assembly 30, and one pair 25 is dedicated to the transmitter assembly 20. Each pair carries power and digital control signals from the system controller 50 to its respective transmitter or receiver assembly 20, 30. Additionally, the receiver pair 34 returns an analog receiver signal to system controller 50. A third pair 24 carries a control signal from the system controller 50 that illuminates a red/green indicator LED 21 located on the transmitter assembly 20.

Figure 9:
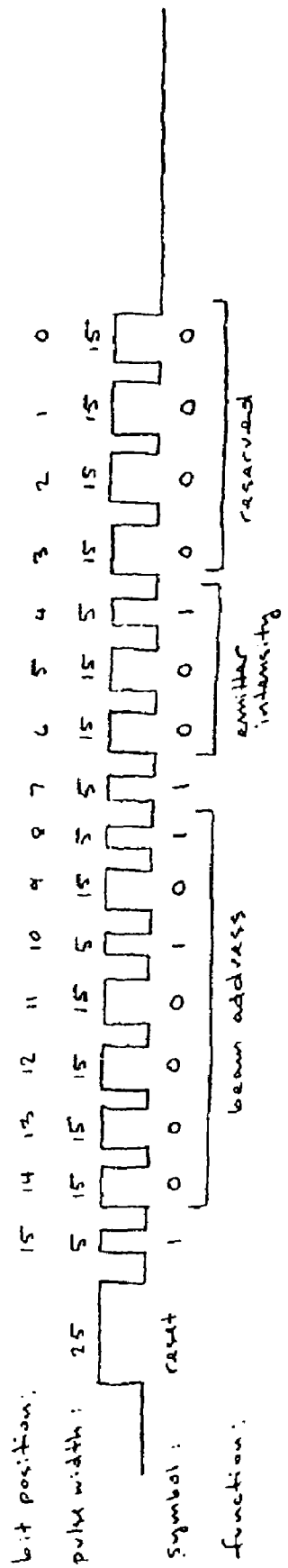
FIG. 9 is a graphical depiction of a communication protocol of a preferred embodiment.

The system controller 50 preferably communicates with the transmitter assembly 20 and the receiver assembly 30 by way of a digital pulse train, and one preferred embodiment of a suitable pulse train is shown in FIG. 9. For example, the system controller 50 can control the activation and deactivation of the light sources 23 and the light receivers 33, as well as the intensity of the light generated by the light sources 23. This enables the light sources 23 to be sequentially activated, one at a time, so that the transmitter-receiver pairs can be sequentially interrogated. The pulse train is preferably composed of pulses of three different widths representing, respectively, a start bit, a logic zero, and a logic one. The pulse train is periodically sent to the receiver assembly 30 and transmitter assembly 20 to activate a specific transmitter-receiver pair to enable interrogation of the specific light beam corresponding to the transmitter-receiver pair. The pulse train begins with a start bit, followed by a series of data bits—typically sixteen. The currently preferred configurations allocate seven data bits to the light beam address decoder and three bits to the current source, with the remaining bits reserved for future use.

In the example shown in FIG. 9, bits 15 and 7 are always "1" in order to activate the lock-out circuits. Also, in this example, the beam address is "5" and the emitter intensity is "1". The beam address values are used to active the light transmitters and light receivers, and the emitter intensity value is used to set the intensity level of the light emitted from the light sources. Further, the pulse widths are denominated in microseconds, and the interval between pulses is five microseconds. While a preferred, serial communication technique and protocol are described and shown herein, various other types of communication techniques and protocols, such as serial and parallel, can be used herewith, as known by those skilled in the art.

Figure 7:
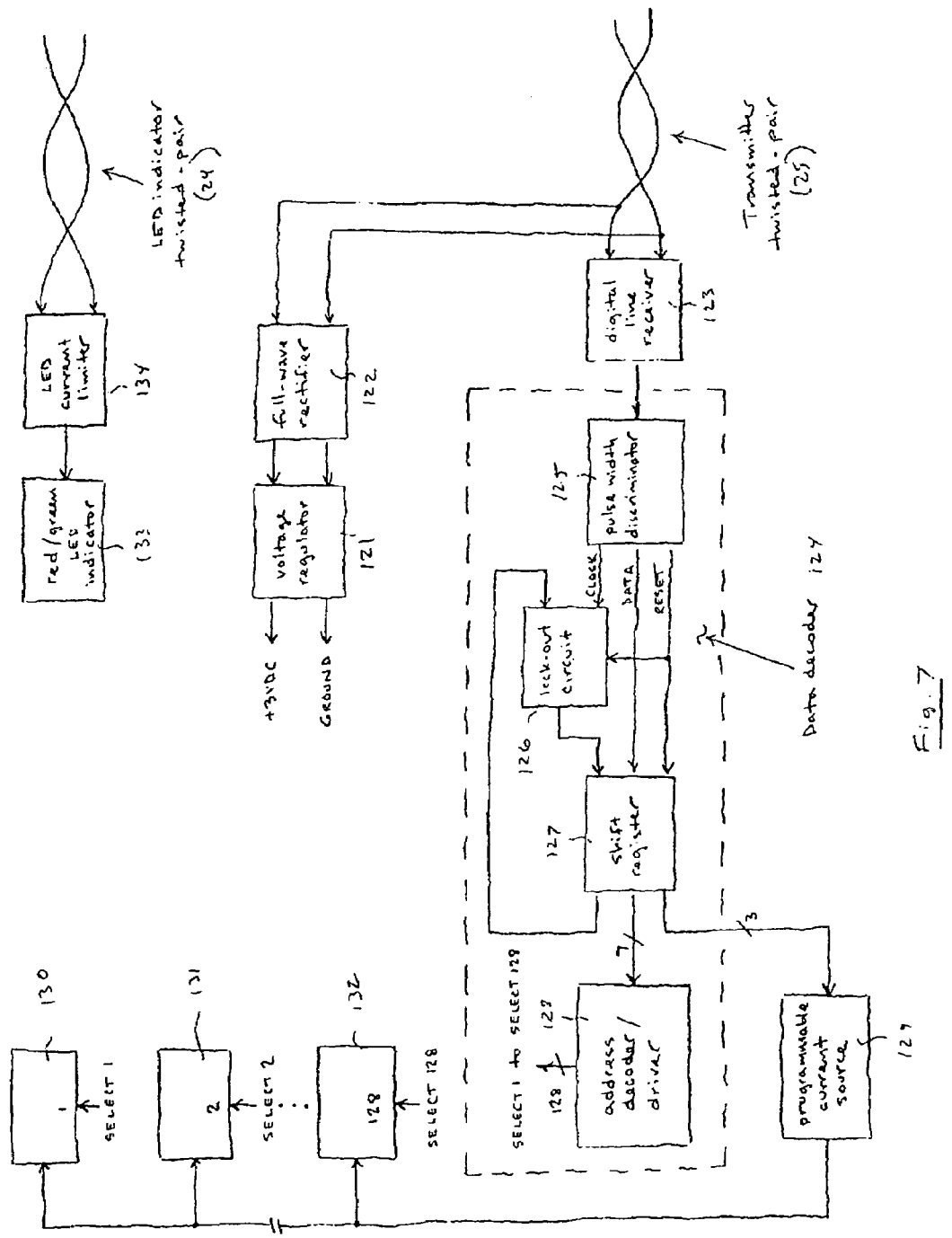
FIG. 7 is a block diagram of a transmitter assembly of a preferred embodiment.

The transmitter and receiver assemblies 20, 30 preferably contain components that enable the transmitter and receiver assemblies 20, 30 to perform lower-order control and signal processing functions. As shown in FIG. 7, the transmitter assembly 20 preferably comprises a voltage regulator 121, a full-wave rectifier 122, a digital line receiver 123, a data decoder 124, an address decoder/light source driver 128, a programmable current source 129, an LED current limiter 134, and an indicator 133.

The voltage regulator 121 derives a full-wave rectified and regulated bus voltage from the raw voltage present on the twisted-pair cable 25 that connects the transmitter assembly 20 to the system controller 50. This regulated voltage powers all circuits located within the transmitter assembly 20.

The digital line receiver 123 and data decoder 124 receive and decode a digital pulse train generated by the system controller 50. The light beam address and the digital current source input value are both derived from the decoded pulse train, which is periodically sent to the receiver assembly 30 and transmitter assembly 20 to configure them for interrogation of a specific light beam. This enables the light sources 23 to be sequentially activated, one at a time, so that the transmitter-receiver pairs can be sequentially interrogated. The digital line receiver 123 uses a differential-input comparator to convert the differential pulse train received from the system controller 50 into a single-ended signal compatible with standard digital logic devices. The data decoder 124 contains a pulse width discriminator 125, a shift register 127, and address decoder circuit 128. The digital line receiver's output is connected to the pulse width discriminator's input. The discriminator 125 has reset, data, and clock outputs. The reset output pulses in response to a start bit pulse, the data output assumes a logic low or logic high level in response to logic zero and logic one pulses, and the clock output pulses in response to the trailing edge of every logic zero or logic one pulse. The reset, data, and clock outputs are connected to a shift register 127 that converts the serial data stream into a sixteen bit parallel word. Seven of these bits are connected to an address decoder 128 that, in current configurations, may have up to 128 outputs capable of selecting one of 128 transmitter-receiver pairs in response to the seven bit address presented to its input.

The transmitter assembly 20 uses the address decoder outputs to directly enable one of up to 128 light sources to be activated, which are represented by the three depicted light sources 130, 131, 132. The light sources 130, 131, 132 are preferably two-terminal devices, and the second terminal of each light source is tied to a common bus connected to the output of the digitally programmable current source 129.

The transmitter data decoder 124 has a lock-out feature that inhibits the shift register clock after the sixteenth data bit has been received. After transmitting the start bit and sixteen data bits, the system controller 50 preferably transmits a ten cycle 208 kHz pulse train to modulate the selected light source. The lock-out circuit 126 prevents alteration of the decoded data word by the light source modulation pulses or by any other spurious pulses. The lock-out circuit 126 releases the shift register clock only after it receives a reset pulse. The light emitted from the light sources 23 is modulated to minimize interference from artificial and natural lighting. This technique modulates the light source drive signals at a frequency of approximately 208 kHz, which, in turn, modulates the intensity of emitted infrared light. Other modulation frequencies can be used, as well as non-modulated light transmissions.

The programmable current source 129 has a common connection to all light sources, although the programmable 129 effectively supplies current only to the one light currently selected by the address decoder/driver 128. The programmable current source 129 obtains its digital input from the data decoder, as described above, which enables it to establish the maximum intensity of the infrared light emitted by the light sources 23. This adjustment enables the system to accommodate variations in the signal level generated by the different transmitter-receiver pairs, which can result from manufacturing variability and from the differences in the gap widths that can be implemented between the transmitter assembly 20 and the receiver assembly 30. In general, the received signal level declines as gap width increases, and the programmable current source 129 can be adjusted to compensate for the different gap widths. Optimizing the intensity of the infrared light emitted by the light sources 23 reduces the dynamic range of the signal levels processed by the system, increases the system's signal-to-noise ratio, and may also reduce complexity and cost of the signal processing circuits. For example, if dynamic range is reduced it may be possible to use a low-cost eight bit analog-to-digital converter rather than a more expensive twelve bit converter.

In a preferred embodiment, a single calibrated intensity value is used for all light sources. However, if the ratio of the highest to the lowest received signal levels exceeds more than about 1.5 then it may be advantageous to establish a unique calibrated intensity value for each light source because excessive disparity between the strongest and weakest light beams may degrade measurement resolution to an unacceptable level whenever the weaker light beams are active.

To determine whether an unacceptable disparity is present, the system can implement a calibration procedure. The calibration procedure incrementally adjusts the current source's digital input, beginning with its lowest setting, until the receiver signal level reaches approximately 80% of the analog-to-digital converter's full scale input range. The 20% headroom prevents immediate saturation of the analog-to-digital converter input in the event that environmental conditions cause an increase in signal level. The calibrated digital intensity value is then stored in non-volatile read-write memory for use in all subsequent light beam interrogations. If a unique calibrated intensity value is to be found for each light source then the calibration procedure will repeat this algorithm for each light source. If only one common calibrated intensity value is to be found for all light sources then the calibration procedure will sequentially examine all light receivers and compare each signal level with the 80% target level before incrementing the current source's digital input. As soon as any light source signal reaches the 80% target level, the calibration procedure will store the current intensity value in non-volatile read-write memory then terminate.

Figure 8:
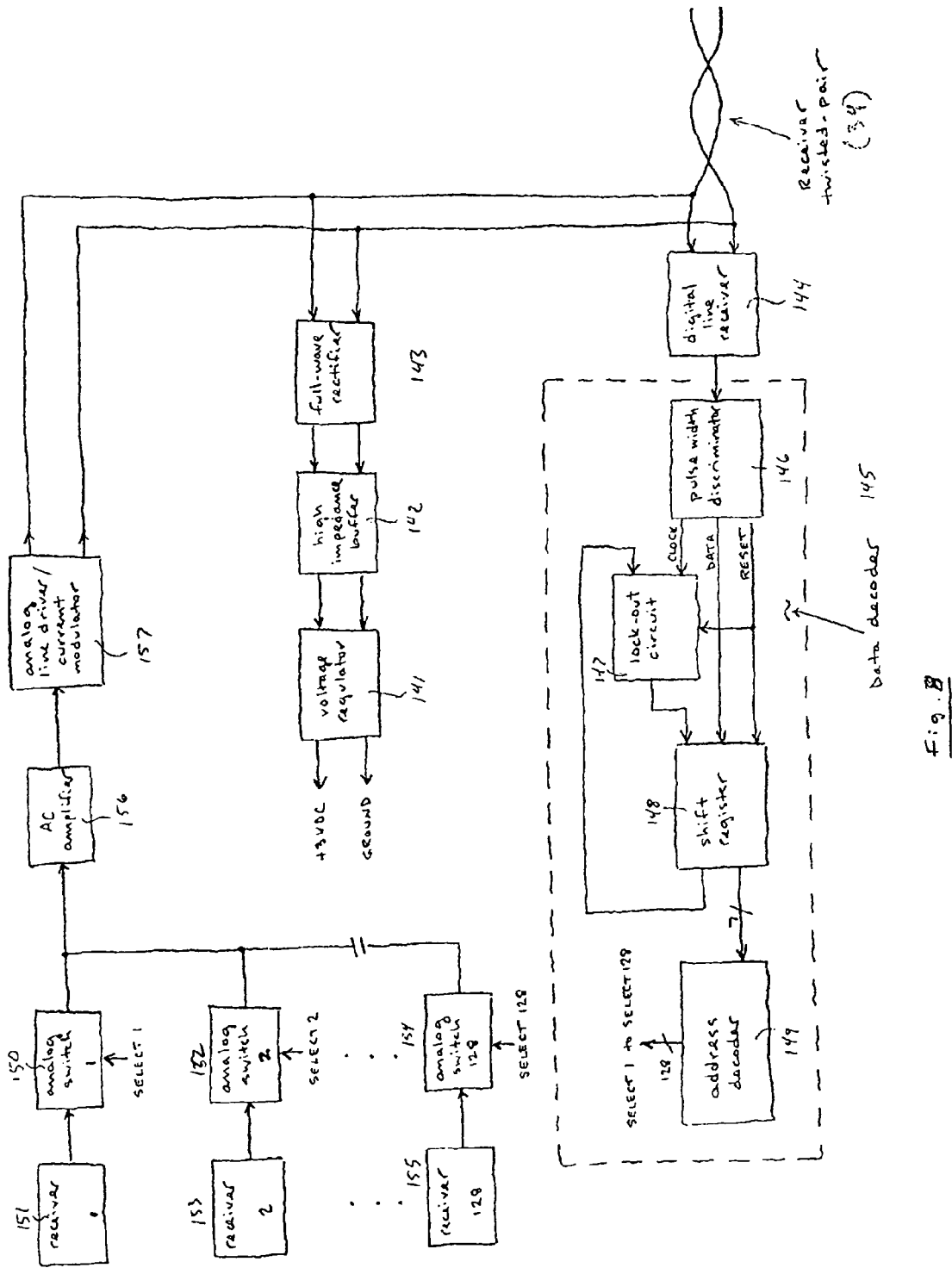
FIG. 8 is a block diagram of a receiver assembly of a preferred embodiment.

As shown in FIG. 8, the receiver assembly 30 preferably comprises a voltage regulator 141, a digital line receiver 144, a data decoder 145, a plurality of analog switches 150, 152, 154, an AC amplifier 156, and an analog line driver 157.

The voltage regulator 141 derives a full-wave rectified and regulated bus voltage from the raw voltage present on the twisted-pair cable 34 that connects the receiver assembly 30 to the system controller 50. This regulated voltage powers all circuits located within the receiver assembly 30. In addition, the input of the voltage regulator 141 along with the high impedance buffer 142 and the full-wave rectifier 143 are configured to present a high impedance to the analog line driver 157 that transmits the amplified receiver signal to the system controller 50 to prevent distortion and attenuation of this signal.

The digital line receiver 144 and data decoder 145 receive and decode a digital pulse train generated by the system controller 50. The light beam address is derived from the decoded pulse train, which is periodically sent to the receiver assembly 30 and transmitter assembly 20. This enables the light receivers 33 to be sequentially activated, one at a time, so that the transmitter-receiver pairs can be sequentially interrogated.

The digital line receiver 144 uses a differential-input comparator to convert the differential pulse train received from the system controller 50 into a single-ended signal compatible with standard digital logic devices. The data decoder 145 contains a pulse width discriminator 146, a shift register 148, and an address decoder circuit 149. The digital line receiver's output is connected to the pulse width discriminator's input. The discriminator 146 has reset, data, and clock outputs. The reset output pulses in response to a start bit pulse, the data output assumes a logic low or logic high level in response to logic zero and logic one pulses, and the clock output pulses in response to the trailing edge of every logic zero or logic one pulse. The reset, data and clock outputs are connected to a shift register 148 that converts the serial data stream into a sixteen bit parallel word. Seven of these bits are connected to an address decoder that, in current configurations, may have up to 128 outputs capable of selecting one of 128 transmitter-receiver pairs, which are represented by the three light sources 130, 132, 132 and the three light receivers 151, 153, 155 shown in FIGS. 7 and 8, in response to the seven bit address presented to its input.

The receiver assembly 30 uses the address decoder outputs to enable one of up to 128 analog switches to be activated, which are represented by the three switches depicted as 150, 152, 154. The input of each switch 150, 152, 154 is connected to a light receiver 151, 153, 155, and the output of each switch 150, 152, 154 is connected to a common receiver signal bus. The bus terminates at the input of the AC amplifier 156. The output of the amplifier 156 is connected to the analog line driver 157 which modulates the overall current drawn from the twisted-pair cable 34 in proportion to the amplified signal. This modulated current is detected by the system controller 50 and is converted into a voltage for further processing.

The receiver data decoder circuit 145 has a lock-out feature that inhibits the shift register clock after the sixteenth data bit has been received. After transmitting the start bit and sixteen data bits, the system controller 50 preferably transmits a ten cycle 208 kHz pulse train to modulate the selected light source. The lock-out circuit 147 prevents alteration of the decoded data word by the light source modulation pulses or by any other spurious pulses. This feature is implemented in a preferred embodiment because the same data stream is preferably sent from the system controller 50 to the transmitter assembly 20 and the receiver assembly 30. However, the different data streams could be implemented for transmission to the transmitter assembly 20 and the receiver assembly 30, respectively. The lock-out circuit 147 releases the shift register clock only after it receives a reset pulse.

Figure 6:
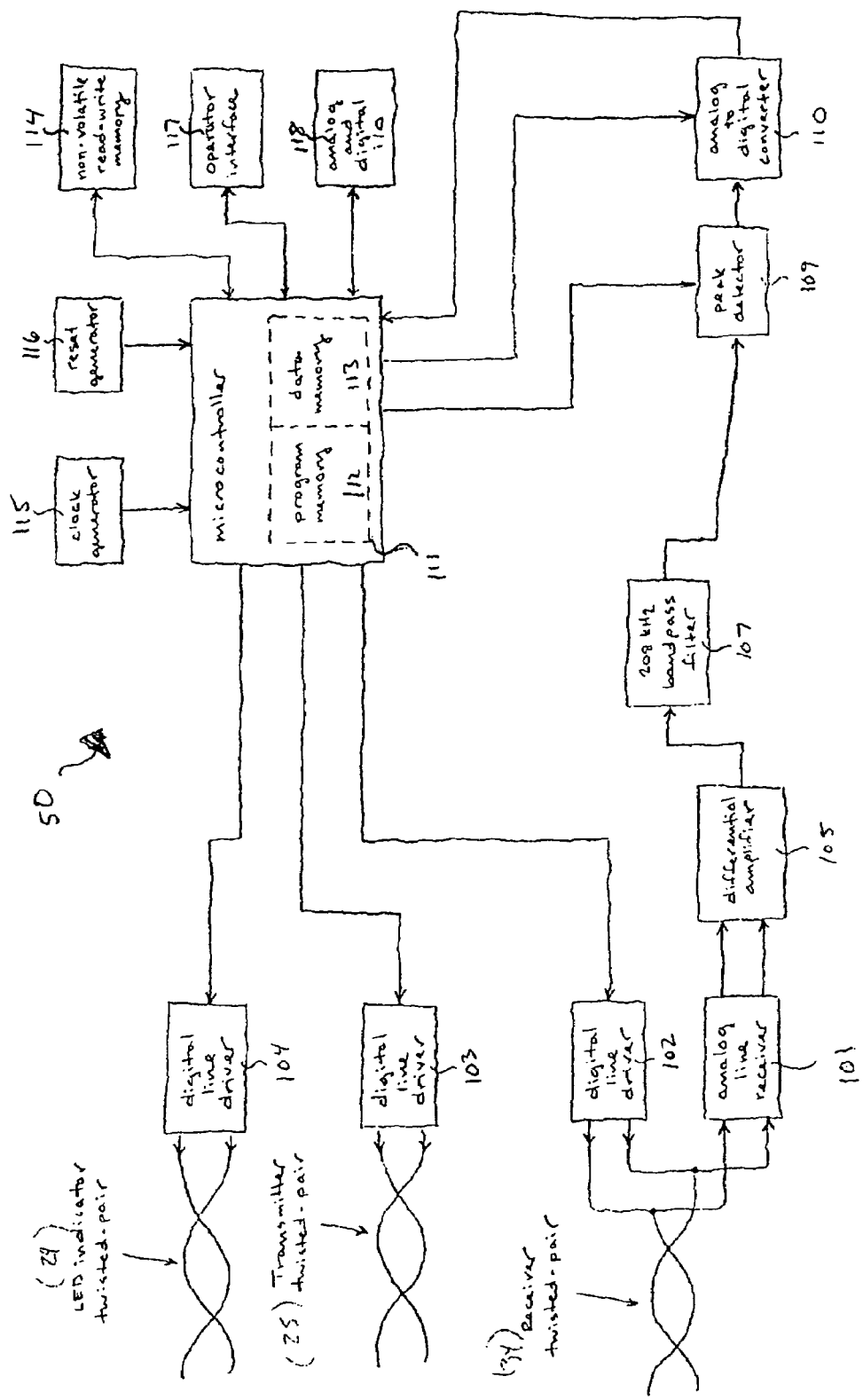
FIG. 6 is a block diagram of a system controller of a preferred embodiment.

In operation, the light receivers 33 receive modulated light and convert the received light into an electrical signal that is routed through several frequency-limiting filter stages, including a first-order high pass filter (not shown) that is preferably located immediately before the AC amplifier 156 and a second-order band-pass filter 107 (FIG. 6) that is preferably located before the peak-detector 109 (FIG. 6). The high-pass filter removes all DC signal components which are primarily the result of incandescent lighting, direct sunlight, and other natural light. These DC components are generally very large, so eliminating them greatly increases the dynamic range available in subsequent signal processing stages for the signal of interest. The band-pass filter 107 further limits the range of signal frequencies admitted, eliminating low frequency flicker generated by fluorescent lamps, high-pressure gas discharge lamps, and other types of artificial lighting.

The signal generated by the receiver assembly 30 is indicative of the position of the edge of the web and is used by the system controller 50 to determine the position of the edge of the web. The amount of light received by a light receiver is proportional to the amount of occlusion caused by the web and the signal generated by the receiver assembly 30 is proportional to the amount of light received by the light receivers. A graphical depiction of the relationship between the light received by a single light receiver and the amount of occlusion of the corresponding light beam is shown in FIG. 10.

Figure 10:
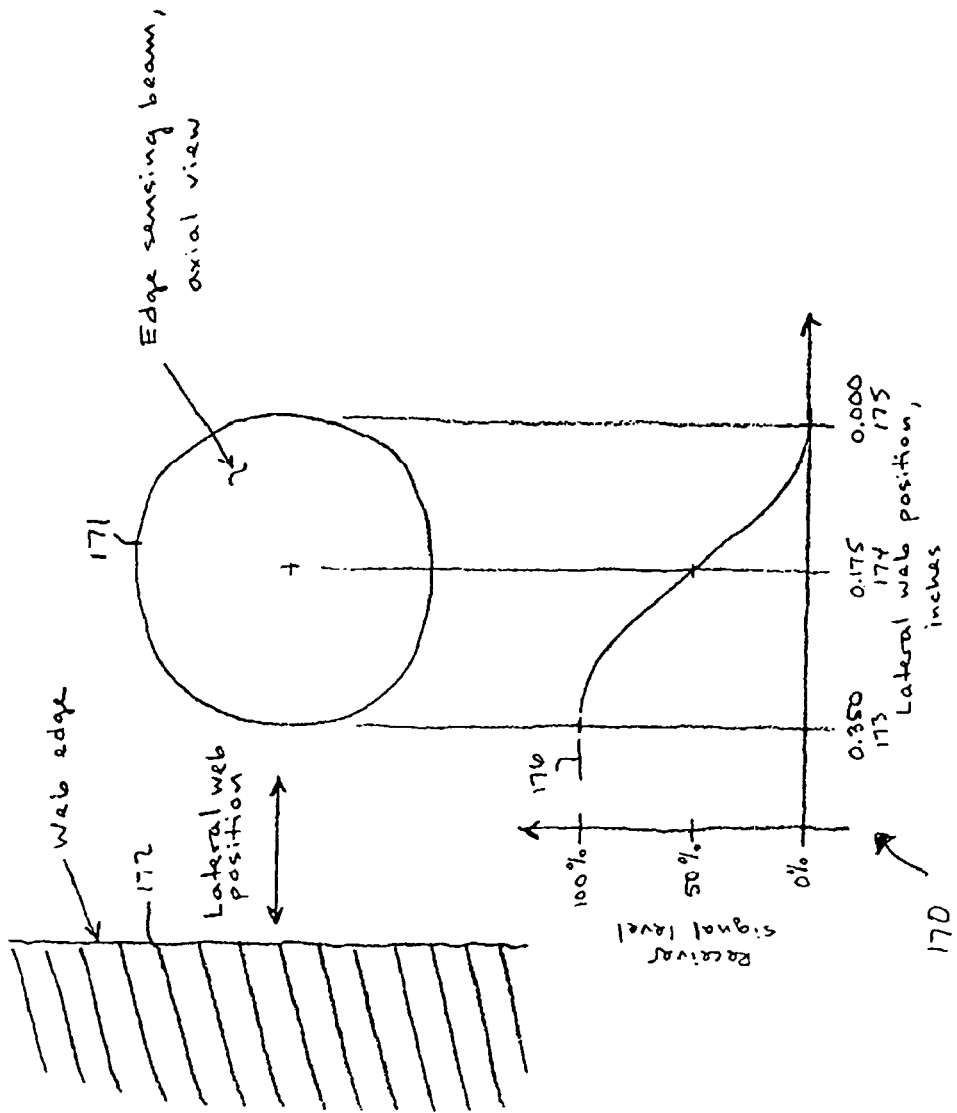
FIG. 10 is a graphical depiction of a received signal strength for a single light receiver as compared to a lateral position of an edge of a web of a preferred embodiment.

FIG. 10 shows a graph 170 that depicts the interrelationship between a beam of light 171 and an edge of a web 172. The x-axis of the graph 170 shows the lateral position of the web, shown in this example as inches from the right side of the light beam. The y-axis of the graph 170 shows the signal level of the light received by a light receiver. Line 176 is the graphical depiction of the interrelationship between the x and y values. When the web 172 is in a position whereby is does not occlude any of the light in the light beam, the signal level of the light beam, as received by the receiver, is 100%. As the web 172 moves to the right, it will occlude some or all of the light beam, resulting in a decreased signal level being received by the light receiver. In turn, the signal generated by the receiver assembly 30 changes and the signal level received by the light receiver changes.

The system controller 50, the transmitter assembly 20, and the receiver assembly 30 can compute a lateral web position measurement from the signals generated by the receiver assembly 30. In the preferred embodiment, the system controller 50 sequentially interrogates one transmitter-receiver pair at a time, beginning with the pair furthest from the web, pair 1, until it locates the edge of the web. During interrogation of each pair the light source is activated and the signal level generated by the light receiver is measured. Edge detection occurs when the system controller 50 finds an transmitter-receiver pair that is producing a signal level indicating partial occlusion of its light beam.

Once the edge is detected, the system controller 50 then switches to a second interrogation pattern that, preferably, sequentially interrogates the two pairs closest to the edge of the web one at a time. The numerical position of these two pairs within the array provides coarse position information and analog interpolation of their signal levels provides fine position information. The coarse and fine position information is combined by the system controller 50 into one high resolution position measurement that has a range limited only by the number of transmitter-receiver pairs employed.

The use of two signal levels to determine fine position confers several important advantages over other techniques that use only one. Foremost is the absence of abrupt discontinuities in the computed position of the web as it moves laterally and causes activation of new pairs that are closer to the edge and deactivation of pairs that are further from the edge. This is accomplished by using a weighted average of the signal levels generated by the two pairs, which is described in more detail below. In general, the weighting is adjusted dynamically as the edge moves. The closer the edge comes to a given pair, the more weight that pair is given in the average—and the less weight given to the other pair. The width of the transition region in which weight shifts entirely from one pair to the other is approximately one quarter of the width of a light beam. When the edge is outside of this region full weight is given to the pair closest to the edge.

A second advantage of this technique is reduction in non-linearity resulting from the nonlinear characteristics of the individual light beams. The circular cross-sectional shape of the sensing light beams and the non-uniform distribution of energy within them result in a sigmoidally shaped plot of signal level versus edge position. Using the weighted average of two adjacent light beams produces a significantly more linear position measurement than using only one.

Due to manufacturing variations in the electronic light source and light receivers, signal routing circuits and optics, the signal levels produced by the transmitter-receiver pairs under identical conditions may vary from one pair to the next. A normalization procedure occurs immediately after interrogation of each pair that eliminates the variations that would otherwise introduce errors into the computed position measurements. This step normalizes the raw signal measurement with calibration values pre-recorded during calibration of the edge detector. The calibration procedure sequentially measures the un-occluded signal level of each transmitter-receiver pair and records it in non-volatile read-write memory.

Figure 11A:
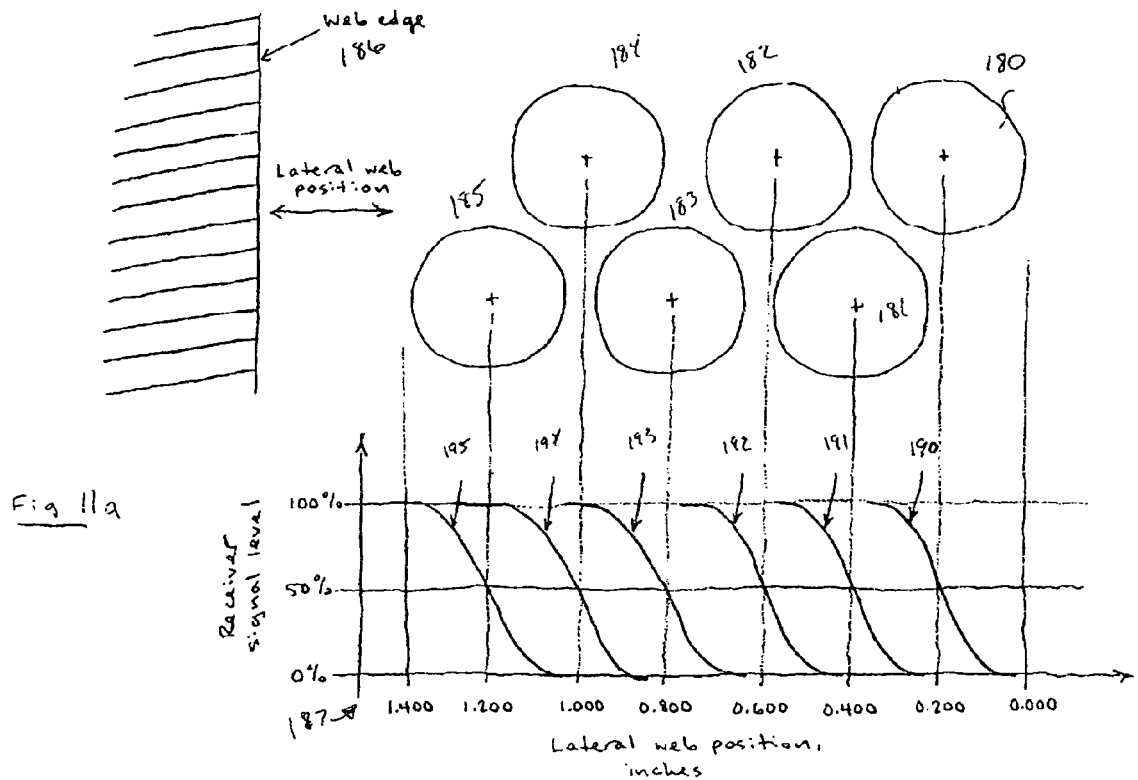
FIG. 11a is a graphical depiction of received signal strengths for a plurality of light receivers as compared to a lateral position of an edge of a web of a preferred embodiment.
Figure 11B:
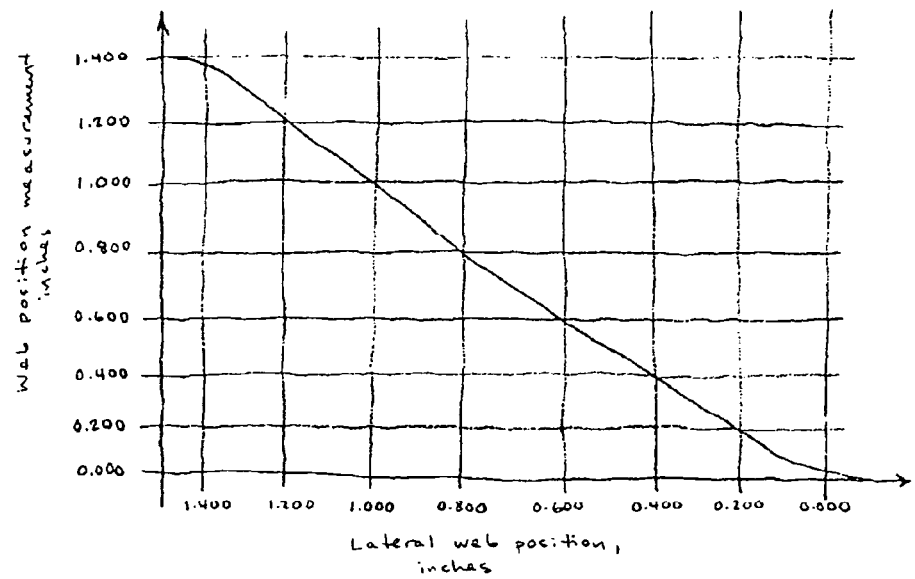
FIG. 11b is a graphic depiction of a calculated lateral position of an edge of a web as compared to an actual lateral position of an edge of a web.

FIGS. 11a and 11b depict an example of how six transmitter-receiver pairs can be used together to determine the lateral position of an edge of a web.

FIG. 11a depicts 6 light beams of light 180-185 and the edge of a web 186. FIG. 11a also depicts a graph 187 that shows the graphical relationships 190-195 between the signal level received for each of the light beams 180-185, respectively, as compared to the lateral position of the edge of the web 186. For example, if the web were to move towards the right so that the edge was at the middle of light beam 183, the graph 187 shows that the signal level for the light receivers associated with light beams 184 and 185 would be 0%, the signal level for the receiver associated with light beam 183 would be 50%, and the signal level for the light receivers associated with light beams 180-182 would be 100%. This information can be used to determine that the edge of the web 186 is 0.8 inches from a reference point at the right side of FIG. 11a. FIG. 11b graphically depicts the calculated position of the edge of the web, using the systems and methods described herein, as compared to the actual position of the web.

In another example, the edge of the web 186 is located midway between the centers of light beams 183 and 184, which means that a portion of both light beams 183 and 184 is occluded. In this example, the signal level for the receiver associated with light beam 185 would be 0% and the signal level for the light receivers associated with light beams 180-182 would be 100%. The signal level for both of the light receivers associated with light beams 183 and 184 will be between 0% and 100%.

In this example, the lateral position of the web can be determined by using a weighting function, as depicted in FIGS. 12*a*-12*e*. FIG. 12*a* shows a graph of the signal strength 194 from FIG. 11*a*, and FIG. 12*b* shows a graph of the signal strength 193 from FIG. 11*a*. Due to the physical position of light beams 183 and 184, there will be some overlap. Points 196 and 197 in FIG. 12*b* denote the region in which a weighting function is used in conjunction with signals 193 and 194 to determine the lateral position of the web edge. FIG. 12*c* depicts the weighting that is applied to signal 194, as the web moves laterally, and FIG. 12*d* depicts the weighting that is applied to signal 193, as the web moves laterally. At point 196, only the signal 194 is used, and at point 197 only the signal 193 is used. In between points 196 and 197 different proportions of signals 193 and 194 will be used as depicted in FIGS. 12*d* and 12*c*, respectively. This allows for the position of the edge of a web to be accurately determined when its position is between or overlaps two of the light beams.

Figure 13:
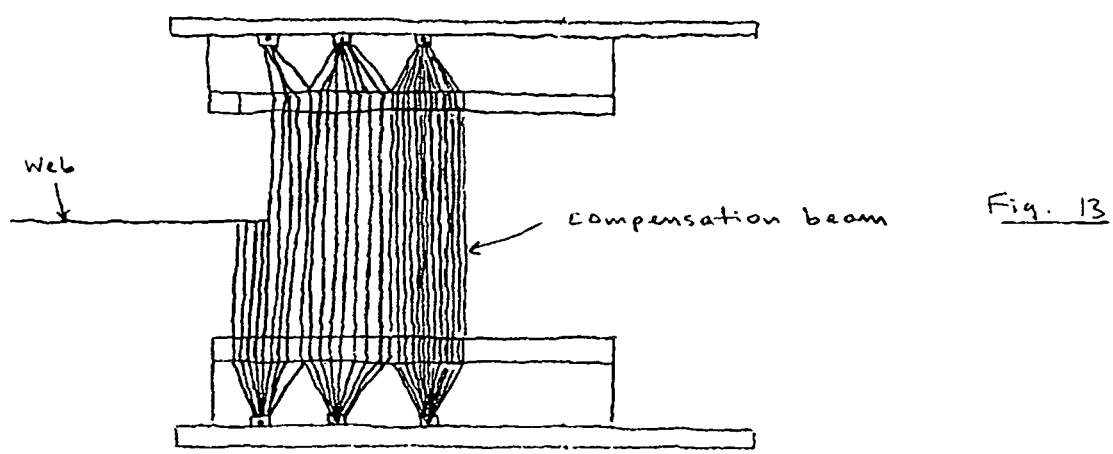
FIG. 13 is a side view of a compensation beam of a preferred embodiment.

Another feature of the edge detector assembly 10 is that it can compensate for several factors that can affect measurement accuracy. These factors include the presence of gas, smoke, or particulate matter, as well as contaminant build-up on exterior surfaces of the optical components and temperature and age induced drift in the light sources, light receivers, control circuits, and signal processing circuits. As shown in FIG. 13, the compensation technique employs a transmitter-receiver pair located near the edge of the web, but located so as not to be occluded by the web, to provide a reference signal that reacts solely to environmental changes and circuit drift and not to web position. The system controller 50 periodically interrogates the compensation pair and uses the measured signal level to adjust the signal measurements taken by the transmitter-receiver pairs that are used to determine the edge position. This adjustment effectively cancels all fluctuation in the edge-sensing signals caused by environmental change and circuit drift.

To improve the effectiveness of the compensation technique, reference level measurements are preferably taken in close proximity to the edge-sensing light beams, and the light sources, light receiver, associated optics, and signal routing and processing circuits are preferably selected to be as near-identical as practicable.

To realize the first objective, the system controller 50 dynamically reconfigures the transmitter-receiver pairs as edge sensing pairs, compensation pairs or idle pairs as needed in order to track the edge of the web and measure ambient conditions near the edge of the web. Typically, the system controller 50 selects the third-most pair away from the edge of the web for use as the compensation pair. In effect, the compensation pair follows the edge sensing pairs as they track the edge of the web. One advantage of this technique is especially apparent in situations where the edge detector is located near the exit of a drying oven and the heat radiated by the hot web creates a substantial temperature differential between the transmitter-receiver pairs closest to the web and those located some distance away from it.

To realize the second objective, the light sources and the light receivers are selected from a single manufacturing lot and are precisely located on their respective printed circuit boards using automated surface-mount assembly techniques; the optics are formed from monolithic lens arrays to minimize assembly-induced mechanical variation; and the receiver's signal routing circuit incorporates a multiplexer to route the multiple raw transmitter-receiver signals into one common amplifier and signal processing circuit.

This multiplexed-input technique minimizes parallel or duplicate signal paths that may respond differently to environmental changes and aging. While multiple receiver elements and analog switches are used in this particular implementation of the receiver assembly, all subsequent signal processing steps are performed by one common signal processing circuit. Changes in the performance of the common circuit affect the processed edge-sensing and compensation signals equally and will, therefore, be cancelled by the compensation algorithm and will have no affect on the computed position measurement.

In one embodiment, system controller 50 can be used to alter the position of web by communicating with a web mover, such as a steering roll, a positive displacement guide, an unwind stand, and a rewind stand, as known by those skilled in the art. In another embodiment, the system controller 50 can be used in conjunction with a process monitoring or measurement system, as known by those skilled in the art.

All of the components that comprise the transmitter assembly 20, the receiver assembly 30, and the system controller 50 are well known by those skilled in the art and are readily available from numerous sources. For example, one preferred light source is Optek's light emitting diode, part no. QPR5200. Another preferred light source is Agilent's light emitting diode, part no. HSDL 4400. Also, one preferred light receiver is Optek's phototransistor, part no. OPR 5500. Another preferred light receiver is Agilent's photodiode, part no. HSDL 5400. In addition, a lens array including Fresnel lenses, such as the one described above, are available from Fresnel Technologies, Inc.

All of the functions of the system controller are preferably controlled by a software program that is implemented in the system controller 50. One suitable software program is represented by the pseudo code/flow charts listed in Appendix A, which is attached hereto. Appendix A includes a main program routine and subroutines A-J. The program can be stored in memory included within the system controller 50 or it can be stored in an external memory.

In an alternative configuration, many of the higher-order functions presently implemented in the system controller 50 can be implemented within the transmitter and receiver assemblies, including the band-pass filter, peak detector, microcontroller (processor) and non-volatile read-write memory. In this configuration, one of the twisted-pairs could be eliminated, and the other two twisted-pairs could be dedicated to power and digital data transport, respectively. This configuration would eliminate low-level analog signals on the twisted-pairs (thereby reducing susceptibility to RF interference), would reduce the burden imposed upon the system controller 50 when servicing multiple edge detectors, would likely reduce system cycle time (an important advantage in real-time servo control systems), and would increase the number of edge detectors that could be serviced by one system controller simultaneously.

In a further alternative embodiment, the lens assemblies can comprise a lens holder and a plurality of lenses that are coupled with the lens holder. For example, the lens holder can comprise a piece of material that has several openings formed therein, into which lenses can be inserted or to which lenses could be attached. The lens holder can comprise various types of materials, including plastics, metals, composites, and the like. The lenses can comprise Fresnel lenses, spherical lenses, plano-convex lenses, and bi-convex lenses and can formed from various materials, including plastics and glass, for example.

It is to be understood that a wide range of changes and modifications to the embodiments described above will be apparent to those skilled in the art and are contemplated. It is therefore intended that the foregoing detailed description be regarded as illustrative rather than limiting, and that it be understood that it is the following claims, including all equivalents, that are intended to define the spirit and scope of the invention.

The invention claimed is:

1. A system for use in detecting an edge of a web of material, the system comprising;
   a plurality of light sources being operative to transmit light, the plurality of light sources being arranged in two substantially parallel rows that are offset from one another so as to form a staggered pattern;
   a first plurality of lenses positioned such that each of the first plurality of lenses focuses light transmitted from one of the plurality of light sources;
   a second plurality of lenses positioned such that each of the second plurality of lenses is capable of receiving light focused by one of the first plurality of lenses;
   wherein the first plurality of lenses is spatially separated from the second plurality of lenses such that a gap is formed therebetween and such that only a portion of the web can pass through the gap; and
   a plurality of light receivers positioned such that each of the plurality of light receivers can receive light focused from one of the second plurality of lenses.

2. The system of claim 1, wherein the plurality of light sources comprise light emitting diodes.

3. The system of claim 1, wherein the plurality of light sources are operative to transmit light in the infrared light range.

4. The system of claim 1, wherein the plurality of light sources are operative to transmit light at variable intensities.

5. The system of claim 1, wherein the plurality of light sources are mounted on a single circuit board.

6. The system of claim 1, wherein one of the plurality of light sources is operative to generate a compensation beam of light.

7. The system of claim 1, wherein the first plurality of lenses comprise Fresnel lenses.

8. The system of claim 1, wherein the second plurality of lenses comprise Fresnel lenses.

9. The system of claim 1, wherein the plurality of light receivers comprise phototransistors.

10. The system of claim 1, wherein the plurality of light receivers comprise photodiodes.

11. The system of claim 1, wherein the plurality of light receivers are arranged in a staggered pattern.

12. The system of claim 1, wherein the plurality of light receivers are arranged in two substantially parallel rows.

13. The system of claim 1, wherein the plurality of light receivers are mounted on a single circuit board.

14. The system of claim 1, further comprising a U-shaped housing having an upper arm and a lower arm, wherein the plurality of light transmitters are located in either the upper arm or the lower arm and the plurality of light receivers are located in the other arm.

15. The system of claim 1, further comprising a controller coupled with the plurality of light sources and the plurality of light receivers.

16. The system of claim 15, wherein the controller is operative to sequentially activate the plurality of light sources and light receivers so that only a single light source and a single light receiver are active at a time.

17. The system of claim 15, further comprising a web guide coupled with the controller.

18. The system of claim 15, wherein the controller detects the edge of the web in response to the light received by the plurality of light receivers.

19. A system for use in detecting an edge of a web of material, the system comprising;
   a plurality of light sources that each transmits light along an axis, the plurality of light sources being arranged in two substantially parallel rows that are offset from one another so as to form a staggered pattern;
   a first plurality of lenses being positioned such that each of the first plurality of lenses is substantially on one of the axes;
   a second plurality of lenses positioned such that each of the second plurality of lenses is substantially on one of the axes;
   wherein the first plurality of lenses is spatially separated from the second plurality of lenses such that a gap is formed therebetween and such that only a portion of the web can pass through the gap; and
   a plurality of light receivers positioned such that each of the plurality of light receivers is substantially on one of the axes.

20. The system of claim 19, wherein the plurality of light sources comprise light emitting diodes.

21. The system of claim 19, wherein the plurality of light sources are operative to transmit light in the infrared light range.

22. The system of claim 19, wherein the plurality of light sources are operative to transmit light at variable intensities.

23. The system of claim 19, wherein the plurality of light sources are mounted on a single circuit board.

24. The system of claim 19, wherein one of the plurality of light sources is operative to generate a compensation beam of light.

25. The system of claim 19, wherein the first plurality of lenses comprise Fresnel lenses.

26. The system of claim 19, wherein the second plurality of lenses comprise Fresnel lenses.

27. The system of claim 19, wherein the plurality of light receivers comprise phototransistors.

28. The system of claim 19, wherein the plurality of light receivers comprise photodiodes.

29. The system of claim 19, wherein the plurality of light receivers are arranged in a staggered pattern.

30. The system of claim 19, wherein the plurality of light receivers are arranged in two substantially parallel rows.

31. The system of claim 19, wherein the plurality of light receivers are mounted on a single circuit board.

32. The system of claim 19, further comprising a U-shaped housing having an upper arm and a lower arm, wherein the plurality of light transmitters are located in either the upper arm or the lower arm and the plurality of light receivers are located in the other arm.

33. The system of claim 19, further comprising a controller coupled with the plurality of light sources and the plurality of light receivers.

34. The system of claim 33, wherein the controller is operative to sequentially activate the plurality of light sources and light receivers so that only a single light source and a single light receiver are active at a time.

35. The system of claim 33, further comprising a web guide coupled with the controller.

36. The system of claim 33, wherein the controller detects the edge of the web in response to the light received by the plurality of light receivers.

* * * * *